US010806916B2

(12) United States Patent
Mantell et al.

(10) Patent No.: US 10,806,916 B2
(45) Date of Patent: Oct. 20, 2020

(54) SYSTEM FOR IDENTIFYING THE PRESENCE AND CORRECTNESS OF A MEDICAL DEVICE ACCESSORY

(71) Applicant: Northgate Technologies Inc., Elgin, IL (US)

(72) Inventors: Robert Mantell, Arlington Heights, IL (US); Chip Curtis, West Dundee, IL (US); Steven Weaver, Itasca, IL (US); Eric Andersen, Palatine, IL (US)

(73) Assignee: Northgate Technologies Inc., Elgin, IL (US)

( * ) Notice: Subject to any disclaimer, the term of this patent is extended or adjusted under 35 U.S.C. 154(b) by 194 days.

(21) Appl. No.: 16/124,446

(22) Filed: Sep. 7, 2018

(65) Prior Publication Data

US 2019/0054285 A1 Feb. 21, 2019

Related U.S. Application Data

(63) Continuation of application No. 15/819,131, filed on Nov. 21, 2017, now Pat. No. 10,105,528, which is a (Continued)

(51) Int. Cl.

*A61M 39/10* (2006.01)
*A61M 13/00* (2006.01)

(Continued)

(52) U.S. Cl.

CPC ............. *A61M 39/10* (2013.01); *A61B 90/90* (2016.02); *A61B 90/98* (2016.02); *A61M 13/00* (2013.01);

(Continued)

(58) Field of Classification Search

CPC .................. A61M 39/10; A61M 13/00; A61M 2039/1022; A61M 2039/1044;

(Continued)

(56) References Cited

U.S. PATENT DOCUMENTS 5,460,490 A 10/1995 Carr et al.
5,529,235 A 5/1996 Boiarski et al.

(Continued)

FOREIGN PATENT DOCUMENTS

EP 1 439 026 A1 7/2004
GB 2 369 057 5/2002
WO WO 2006/017334 A2 2/2006

OTHER PUBLICATIONS

Communication from the International Searching Authority dated Apr. 2, 2013, in conjunction with PCT/IB2012/002462.

(Continued)

*Primary Examiner* — Amber R Stiles
(74) *Attorney, Agent, or Firm* — Brinks Gilson & Lione

(57) ABSTRACT

A medical device accessory comprising an interface configured to connect the medical device accessory with a medical device for administration of a medical treatment using the medical device and the medical device accessory, a plurality of electrical contacts proximate the interface, the electrical contacts comprising a lead electrical contact adapted to receive an voltage from a power source associated with the medical device and one or more identifying electrical contacts, and at least one conductor providing an electrical connection between the lead electrical contact and the one or more identifying electrical contacts. An arrangement of the one or more identifying electrical contacts connected to the lead electrical contact identifies a characteristic of the medical device accessory.

21 Claims, 7 Drawing Sheets

Related U.S. Application Data continuation of application No. 15/018,069, filed on Feb. 8, 2016, now Pat. No. 9,849,275, which is a continuation of application No. 13/683,572, filed on Nov. 21, 2012, now Pat. No. 9,283,334.

(60) Provisional application No. 61/563,119, filed on Nov. 23, 2011.

(51) Int. Cl.

| | |
|---|---|
| ***A61B 90/90*** | (2016.01) |
| ***A61B 90/98*** | (2016.01) |
| ***G01F 1/56*** | (2006.01) |
| ***G01K 7/16*** | (2006.01) |
| ***G01L 9/02*** | (2006.01) |
| *A61B 90/00* | (2016.01) |
| *A61B 17/00* | (2006.01) |

(52) U.S. Cl.

CPC ................ *G01F 1/56* (2013.01); *G01K 7/16* (2013.01); *G01L 9/02* (2013.01); *A61B 2017/00482* (2013.01); *A61B 2090/037* (2016.02); *A61B 2090/0814* (2016.02); *A61M 2039/1022* (2013.01); *A61M 2039/1044* (2013.01); *A61M 2205/14* (2013.01)

(58) Field of Classification Search

CPC ........ A61M 2205/14; G01F 1/56; G01K 7/16; G01L 9/02; A61B 90/98; A61B 90/90; A61B 2090/037; A61B 2090/0814; A61B 2017/00482

See application file for complete search history.

(56) References Cited

U.S. PATENT DOCUMENTS

| | | | |
|---|---|---|---|
| 5,604,681 | A | 2/1997 | Koeninger |
| 5,742,718 | A | 4/1998 | Harman et al. |
| 6,077,272 | A | 6/2000 | McCary et al. |
| 6,468,424 | B1 | 10/2002 | Doing et al. |
| 6,497,363 | B1 | 12/2002 | Kelrich |
| 6,626,355 | B2 | 9/2003 | Sasse et al. |
| 6,649,829 | B2 | 11/2003 | Garber et al. |
| 6,685,831 | B2 | 2/2004 | Donig et al. |
| 6,733,495 | B1 | 5/2004 | Bek et al. |
| 6,987,374 | B2 | 1/2006 | Iribe et al. |
| 7,008,362 | B2 | 3/2006 | Fitzgibbon |
| 7,084,696 | B2 | 8/2006 | Erlebacher et al. |
| 7,091,864 | B2 | 8/2006 | Veitch et al. |
| 7,176,030 | B2 | 2/2007 | Faries, Jr. et al. |
| 7,290,940 | B2 | 11/2007 | Boutoussov |
| 7,299,981 | B2 | 11/2007 | Hickle et al. |
| 7,395,166 | B2 | 7/2008 | Plishner |
| 7,568,619 | B2 | 8/2009 | Todd et al. |
| 7,575,381 | B2 | 8/2009 | Boutoussov |
| 7,645,954 | B2 | 1/2010 | Yasuda |
| 7,647,954 | B2 | 1/2010 | Garber et al. |
| 7,869,974 | B2 | 1/2011 | Plishner |
| 7,959,860 | B2 | 6/2011 | Faries, Jr. et al. |
| 7,988,633 | B2 | 8/2011 | Hossack et al. |
| 8,075,514 | B2 | 12/2011 | Butterfield et al. |
| 8,083,669 | B2 | 12/2011 | Murakami et al. |
| 8,118,790 | B2 | 2/2012 | Dacquay et al. |
| 8,172,468 | B2 | 5/2012 | Jones et al. |
| 8,187,184 | B2 | 5/2012 | Muller et al. |
| 8,297,661 | B2 | 10/2012 | Prouix et al. |
| 8,330,579 | B2 | 12/2012 | Kneip et al. |
| 8,333,518 | B2 | 12/2012 | Jones et al. |
| 8,587,410 | B2 | 11/2013 | Potyrailo et al. |
| 9,283,334 | B2 | 3/2016 | Mantell et al. |
| 9,849,275 | B2 | 12/2017 | Mantell et al. |
| 2001/0034506 | A1 | 10/2001 | Hirschman |
| 2005/0118048 | A1 | 6/2005 | Traxinger |
| 2005/0277805 | A1 | 12/2005 | Hatton |
| 2005/0277873 | A1 | 12/2005 | Stewart et al. |
| 2006/0083466 | A1 | 4/2006 | Boutoussov |
| 2006/0224128 | A1 | 10/2006 | Lurvey et al. |
| 2007/0052422 | A1 | 3/2007 | Houldsworth |
| 2007/0100315 | A1 | 5/2007 | Traxinger |
| 2007/0100316 | A1 | 5/2007 | Traxinger |
| 2007/0167943 | A1 | 7/2007 | Janssen et al. |
| 2007/0239148 | A1 | 10/2007 | Scheller |
| 2008/0303728 | A1 | 12/2008 | Lee et al. |
| 2008/0319260 | A1 | 12/2008 | Murakami et al. |
| 2009/0065565 | A1 | 3/2009 | Cao |
| 2009/0069714 | A1 | 3/2009 | Eichmann et al. |
| 2009/0140837 | A1 | 6/2009 | Jennings |
| 2009/0267765 | A1 | 10/2009 | Greene et al. |
| 2009/0270791 | A1 | 10/2009 | Todd |
| 2009/0327715 | A1 | 12/2009 | Smith |
| 2010/0016855 | A1 | 1/2010 | Ramstein et al. |
| 2010/0069939 | A1 | 3/2010 | Konishi |
| 2010/0114095 | A1 | 5/2010 | Janssen et al. |
| 2010/0324368 | A1* | 12/2010 | Mathieu ............ A61B 1/00128 600/131 |
| 2011/0098698 | A1 | 4/2011 | Bek et al. |
| 2011/0111794 | A1* | 5/2011 | Bochenko ............ A61M 39/02 455/556.1 |
| 2011/0196291 | A1 | 8/2011 | Vischer et al. |
| 2011/0270091 | A1 | 11/2011 | Hossack et al. |
| 2011/0315757 | A1 | 12/2011 | Colman et al. |
| 2012/0108937 | A1 | 5/2012 | Todd |
| 2012/0109173 | A1 | 5/2012 | Todd |
| 2012/0177322 | A1 | 7/2012 | Schwandt et al. |
| 2012/0209243 | A1 | 8/2012 | Yan |
| 2013/0123579 | A1 | 5/2013 | Adams |
| 2013/0123687 | A1 | 5/2013 | Vischer et al. |
| 2014/0014729 | A1 | 1/2014 | Colman et al. |
| 2014/0021251 | A1 | 1/2014 | Colman et al. |

OTHER PUBLICATIONS

PCT International Search Report for PCT/IB2012/002462, dated May 28, 2013.

PCT Written Opinion for PCT/IB2012/002462, dated May 28, 2013.

Web page on Usage Tracking and Limit Use of Disposable Medical Device Attachments; http://www.datakeyelectronics.com/medical-usage-tracking-limit-use.html; Accessed Jun. 29, 2010.

International Preliminary Report on Patentability dated May 27, 2014.

Written Opinion of the International Searching Authority dated May 27, 2014.

* cited by examiner 148 150

| LOGIC STATE | LOGIC STATE |
|---|---|
| HIGH | HIGH |
| HIGH | LOW |
| HIGH | FLOATING |
| LOW | HIGH |
| LOW | LOW |
| LOW | FLOATING |
| FLOATING | HIGH |
| FLOATING | LOW |
| FLOATING | FLOATING |

SYSTEM FOR IDENTIFYING THE PRESENCE AND CORRECTNESS OF A MEDICAL DEVICE ACCESSORY

RELATED APPLICATIONS

This application is a continuation of U.S. patent application Ser. No. 15/819,131, filed on Nov. 21, 2017, pending, which is a continuation of U.S. patent application Ser. No. 15/018,069, filed on Feb. 8, 2016, now U.S. Pat. No. 9,849,275, which is a continuation of U.S. patent application Ser. No. 13/683,572, filed on Nov. 21, 2012, now U.S. Pat. No. 9,283,334, which claims the benefit of U.S. Provisional Application No. 61/563,119, filed on Nov. 23, 2011, all of which are incorporated herein by reference.

TECHNICAL FIELD

The present disclosure relates to medical device accessories, and in particular, a system for identifying the presence and correctness of a medical device accessory.

BACKGROUND

In many areas of medical treatment, the transportation of gases or liquids in various treatments is required. Such treatments, for example, include respiratory, surgical, arthroscopic, laparoscopic, urologic, and even subcutaneous applications (e.g., injections, or sub-dermal insufflation). Because of the complexity of medical treatments and the large number of different but occasionally related procedures, there is a high possibility of attaching or hooking up the wrong medical device accessory to a particular medical device for a particular medical treatment. In the case of tubing sets, for example, the conduits can be metal, rigid or flexible plastic, tubes, or even just a needle itself. The tubing sets may also have characteristics specific to a particular medical treatment, such as conduit diameter, length, pressure ratings, temperature ratings, fluid flow ratings, etc. There is often a need to match the proper conduit to the proper medical device (e.g., an insufflator, a pump, etc.) to insure the proper performance of the medical device, or to insure the medical device performs in certain ways.

Furthermore, within the medical field, hospitals, surgicenters, and doctors' offices often re-use tubing sets for the transportation of gases or liquids which were intended for a single use. This practice has safety, health (e.g., infection), and equipment reliability and performance issues. Practitioners will often substitute tubing sets for manufacturer approved and tested tubing sets without an understanding of the resulting consequences. For example, in laparoscopic insufflation, instances have occurred where an insufflator has become contaminated due to the use of a sub-standard tubing set, or the re-use of a tubing set. In such instances, the potential consequences may also include the insufflator measurement system becoming compromised by a restrictive tubing set, or other degradation of the performance of the insufflator.

To address these and other issues, a system for identifying the presence and correctness of a medical device accessory is described herein.

BRIEF SUMMARY

In one aspect, a medical device accessory includes an interface configured to connect the medical device accessory with a medical device for administration of a medical treatment using the medical device and the medical device accessory. A plurality of electrical contacts are proximate the interface. The electrical contacts include a lead electrical contact adapted to receive a voltage from a power source associated with the medical device and one or more identifying electrical contacts. At least one conductor provides an electrical connection between the lead electrical contact and the one or more identifying electrical contacts. An arrangement of the one or more identifying electrical contacts connected to the lead electrical contact identifies a characteristic of the medical device accessory.

In another aspect, a conductor of the at least one conductors is configured for alignment with a severing element associated with the medical device and is mechanically severable upon disconnection of the medical device accessory with the medical device. The characteristic of the medical device accessory that is identified, after disconnection of the medical device accessory with the medical device, is a prior use of the medical device accessory.

In another aspect, the medical device accessory is characterized by an absence of an active component electrically connected to the lead electrical contact. The active component may be a resistor, a fuse, a memory chip, a capacitor, an optical sensor, or a radio-frequency identification component.

In yet another aspect, the characteristic of the medical device accessory that is identified may be an operating parameter of the medical device for operation with the medical device accessory. Alternatively, the characteristic may be a proper connection of the medical device accessory with the medical device. In another alternative, the characteristic may be an identity of the medical device accessory.

In another aspect, the medical device accessory may be a connector configured to connect the medical device with another medical device accessory.

In another aspect, the medical device accessory may include a conduit having a lumen for transporting a fluid.

In yet another aspect, the arrangement of the one or more identifying electrical contacts connected to the lead electrical contact may be adapted to provide the voltage to a controller associated with the medical device.

In another aspect, a medical device accessory includes an interface configured to connect the medical device accessory with a medical device for administration of a medical treatment using the medical device and the medical device accessory. The medical device accessory also includes a lead electrical contact adapted to receive a voltage from a power source associated with the medical device, an identifying electrical contact, and a conductor providing an electrical connection between the lead electrical contact and the identifying electrical contacts. The conductor is configured for alignment with a severing element associated with the medical device and is mechanically severable upon disconnection of the medical device accessory with the medical device to provide an indication of prior use of the medical device accessory.

In a further aspect, a medical device accessory includes an interface configured to connect the medical device accessory with a medical device for administration of a medical treatment using the medical device and the medical device accessory. A plurality of tabs proximate the interface are configured to engage a plurality of corresponding switching elements associated with the medical device upon connection of the medical device accessory with the medical device. An arrangement of the plurality of tabs identifies a characteristic of the medical device accessory.

In yet another aspect, one or more of the plurality of tabs are configured to move one or more of the plurality of corresponding switching elements from a first position to a second position upon connection of the medical device accessory with the medical device.

In another aspect, a tab of the plurality of tabs is breakable upon engagement with one of the plurality of corresponding switching elements. The characteristic of the medical device accessory that may be identified, after disconnection of the medical device accessory with the medical device, is a prior use of the medical device accessory.

In a further aspect, a medical device accessory includes an interface configured to connect the medical device accessory with a medical device for administration of a medical treatment using the medical device and the medical device accessory. A tab proximate the interface is configured to engage and move a corresponding switching element associated with the medical device from a first position to a second position upon connection of the medical device accessory with the medical device. The tab is breakable upon engagement with the switching element to provide an indication of prior use of the medical device accessory.

DETAILED DESCRIPTION

Described herein are systems for identifying the presence and correctness of a medical device accessory. Although the following description refers to specific embodiments where the medical device accessory is a medical tubing set, those skilled in the art will appreciate that the disclosed concepts and principles may be applied to any medical device accessory, and may be embodied in a separate accessory adapted to connect a medical device to another medical device accessory, i.e., as an intermediate connector.

Notably, in one embodiment, the medical device accessory utilizes a voltage or a current, without using any active elements (i.e., a component that in some way changes its state or function, or communicates actively with a device with or without physical contact), and yet provides a way to communicate presence and characteristics of the medical device accessory. One advantage to this approach is the omission of expensive active components such as, for example, resistors, fuses, memory chips, capacitors, optical sensors, radio-frequency identification components, readers/transponders, bar codes, etc. Rather, as explained below, the system can be implemented using inexpensive voltage or current measurement circuitry. This system has in comparison to the prior art, ease of manufacture, very low cost, multiple configurations, no need for complex methods to identify the medical device accessory, an inexpensive means for disabling use of the accessory, basic electronics for measuring voltage or current, and ease of programming using basic binary coding concepts.

Figure 1:
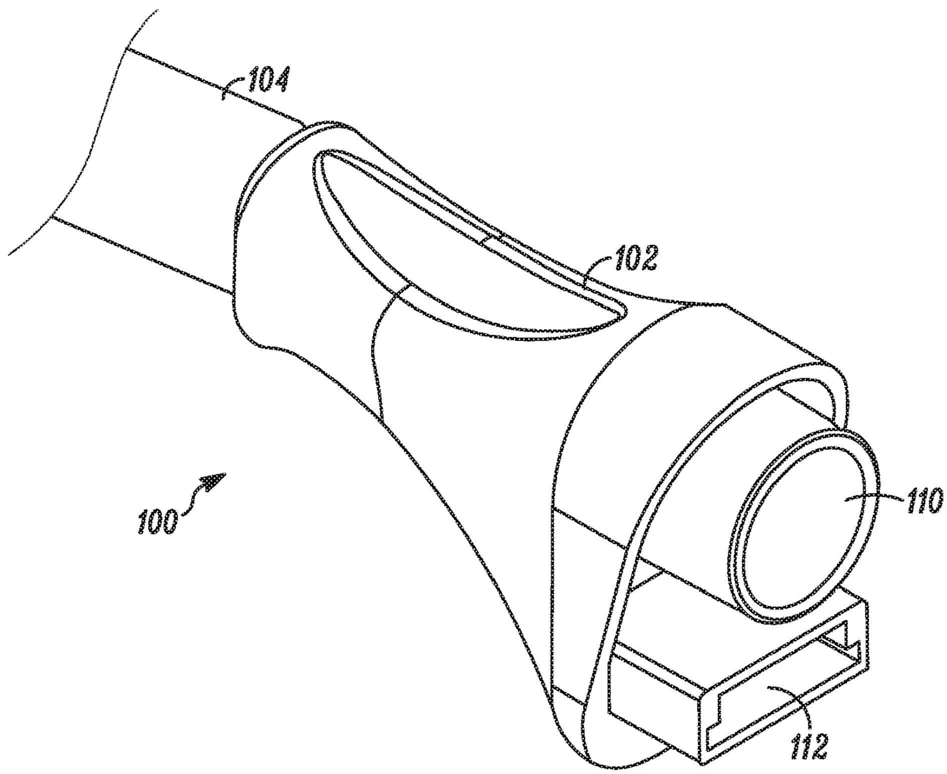
FIG. 1 is a front perspective view of a medical device accessory in the form of a tubing set.
Figure 2:
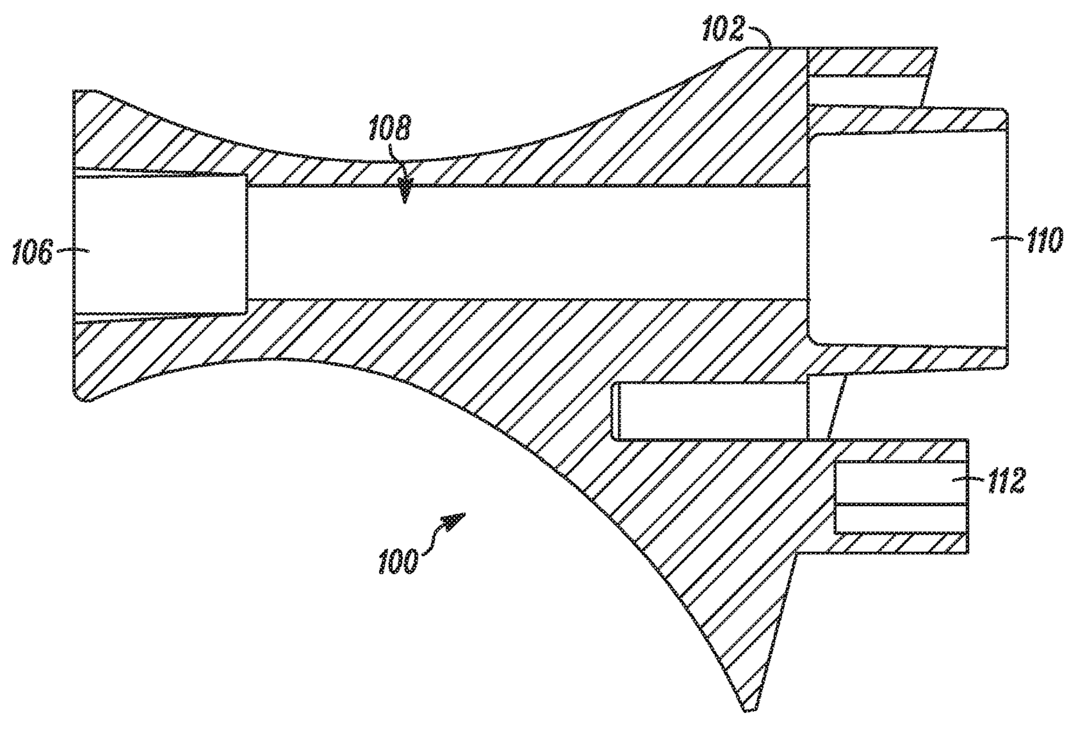
FIG. 2 is a cross-sectional side view of the medical device accessory of FIG. 1.

Referring first to FIGS. 1 and 2, a front perspective view and a cross-sectional side view of a medical device accessory in the form of a tubing set 100 is shown. The tubing set 100 is comprised of a connector 102 disposed at an end of a tube 104. As shown in FIG. 2, the connector 102 may include a female end 106 for receiving the tube 104, a conduit 108 extending through the connector 102, and a male end 110 adapted to engage a suitable corresponding connection on a medical device, for example, a tubing nipple or a luer. Although the connector 102 and the tube 104 are shown as separate components, it is envisioned that the connector 102 may be integrally formed with the medical device accessory. Alternative interfaces for tubing sets could include, for example, quick disconnect, friction fit, luer type, barbed connections, bayonet fittings, etc. It should be appreciated that any suitable interface for connecting a medical device accessory with a medical device may be utilized without departing from the concepts and principles described herein.

Figure 3:
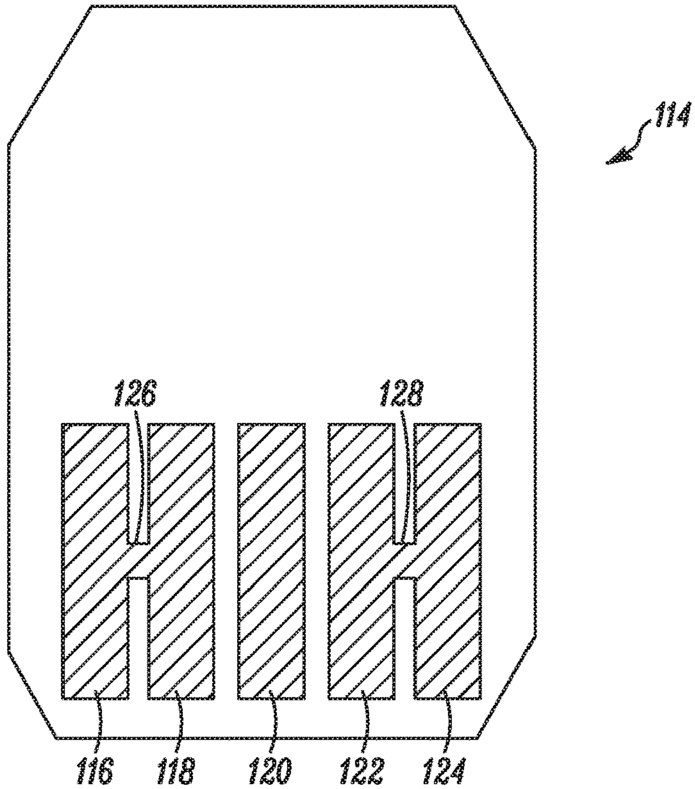
FIG. 3 is a top view of a printed circuit board housed in the medical device accessory of FIG. 1.

The connector 102 further comprises an electrical housing 112. Preferably, the electrical housing 112 is proximate to the interface, i.e. the male end 110 of the connector 102, such that the connection of the medical device accessory with the medical device is unobtrusive. As shown in FIG. 3, an exemplary circuit board 114 is shaped and sized to fit within the electrical housing 112. The circuit board 114 comprises a plurality of electrical contacts designed to engage corresponding electrical contacts on a medical device (not shown). The circuit board 114 further comprises one or more electrical conductors providing an electrical connection between the electrical contacts. As explained below, one or more of the electrical conductors may be severable upon disconnection of the medical device accessory with the medical device, such as for example, by skiving or cutting.

The circuit board 114 shown in FIG. 3 includes five electrical contacts 116, 118, 120, 122 and 124, and two conductors 126 and 128. The conductor 126 provides an electrical connection between the electrical contacts 116 and 118, whereas the conductor 128 provides an electrical connection between the electrical contacts 122 and 124. It is envisioned that the circuit board could include as few as two electrical contacts, or significantly more. Similarly, it is envisioned that any number of electrical conductors could provide an electrical connection between any number of the electrical contacts. Furthermore, it is envisioned that the circuit board 114 could be double-sided, i.e., electrical contacts and conductors printed on both the top and bottom of the circuit board 114, thereby increasing the amount of information provided on a single circuit board.

The tubing set 100 is intended to be used and connected with a medical device adapted to receive the male end 100 of the connector 102, as well as the circuit board 114 and the electrical contacts 116, 118, 120, 122, and 124. For example, the medical device may comprise a plurality of corresponding electrical contacts or pins adapted to create an electrical connection with one or more of the electrical contacts 116, 118, 120, 122, and 124. Furthermore, as explained below in greater detail, the medical device may include a controller and simple circuitry connected to the contacts or pins for reading and determining the presence and correctness of a medical device accessory.

In one embodiment, the system can determine the presence and/or whether the medical device accessory has previously been used. Based on the determination, the system may, for example, provide an indication that the medical device accessory is not present, or that the medical device accessory has previously been used. In this embodiment, the circuit board 114 includes only two electrical contacts and a conductor providing an electrical connection therebetween, for example, electrical contacts 116, 118 and conductor 126 of the circuit board 114 shown in FIG. 3. When a medical device accessory having this configuration is connected with a medical device adapted to receive the medical device accessory, if a voltage is supplied by the medical device at an electrical contact or pin engaged with or corresponding to the electrical contact 116, the medical device can read the voltage at a contact or pin engaged with the electrical contact 118. By periodically providing a voltage at electrical contact 116 and checking for the same voltage at electrical contact 118, the system can determine the presence of a medical device accessory. In other words, when the medical device accessory is connected with the medical device, the circuit formed between electrical contacts 116 and 118 is closed. In this way, the system can determine the presence of a medical device accessory.

Figure 4:
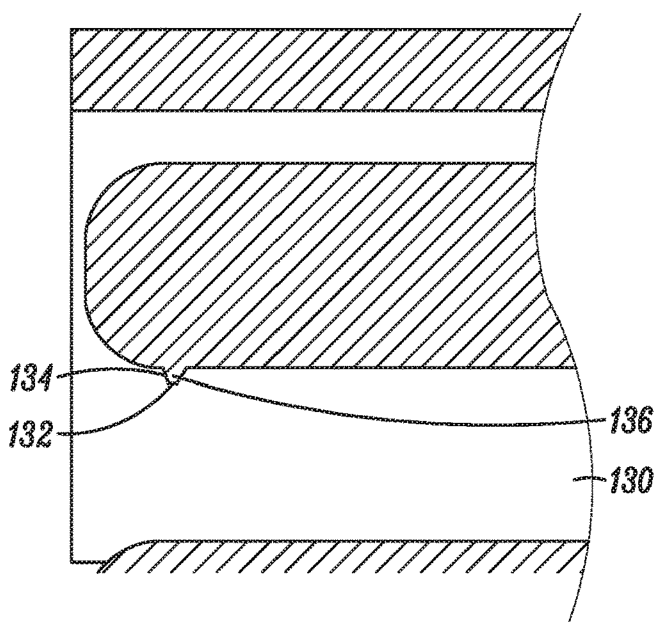
FIG. 4 is a partial cross-sectional view of a port on a medical device adapted for mechanically severing a conductor printed on the circuit board of the medical device accessory upon disconnection of the medical device accessory with the medical device.

In this embodiment, the system may also be able to determine if the medical device accessory has previously been used. For example, as shown in FIG. 4, a partial cross-sectional view of a port 130 on a medical device is adapted for mechanically severing a conductor printed on the circuit board of the medical device accessory upon disconnection from the medical device. The port 130 is disposed on the medical device proximate the interface for connecting the medical device accessory to the medical device, and is adapted to receive, for example, the circuit board 114, the electrical contact 116, 118, and the conductor 126. The port 130 may also house the electrical contacts or pins (not shown) associated with the medical device and which are adapted to engage the electrical contacts 116, 118 on the circuit board 114. The port 130 further comprises a skiving blade 132 positioned and configured to mechanically sever the conductor 126 upon withdrawal of the circuit board 114 from the port 130.

As shown in FIG. 4, the skiving blade 132 comprises a curved front face 134 and a sharp rear edge 136. Accordingly, the skiving blade 132 permits the medical circuit board 114 and the conductor 126 to slide unsevered past the curved front face 134 of the skiving blade 132 upon insertion of the circuit board 114 into the port 130, i.e., connection of the medical device accessory with the medical device, whereas the sharp rear face 136 of the skiving blade 132 mechanically severs the conductor 126 upon withdrawal of the circuit board 114, i.e., disconnection of the medical device accessory with the medical device. It should be appreciated that the conductor could be mechanically severed by any other suitable means, for example, by scribing or cutting. Alternatively, it is envisioned that a small laser (not shown) could be provided within the port 130 for vaporizing a portion of a conductor and breaking the electrical connection between electrical contacts.

In this way the medical device is able to supply a voltage at an electrical contact or pin engaged with or corresponding to the electrical contact 116, and read the voltage at a contact or pin engaged with the electrical contact 118 to determine if the circuit is closed. If the corresponding medical device is adapted to sever the conductor 126 upon disconnection of the medical device accessory with the medical device, an open circuit indicates that the medical device accessory has previously been used. Alternatively, a closed circuit indicates that a medical device accessory is present, and that the medical device accessory has not previously been used.

In a second embodiment, the system is able to determine the presence and/or whether the medical device accessory has previously been used, as well as other characteristics of the medical device accessory. By increasing the number of electrical contacts and using conductor patterns (i.e., reading the arrangement of electrical contacts electrically connected to the electrical contact receiving a voltage from the medical device), the system can identify additional characteristics of the medical device accessory.

In an embodiment where the circuit board 114 includes at least four electrical contacts and two conductors, e.g., electrical contacts 116, 118, 122, 124 and conductors 126 and 128, a code (similar to a binary code) can be used to identify a code associated with the medical device accessory. For example, after the medical device supplies a voltage, an electrical connection, or a closed circuit, between electrical contacts 116 and 118 could represent a binary “1”, and an open circuit between electrical contacts 122 and 124 could represent a binary “0”. Combining the two would produce a binary code of (1, 0). Similarly, a closed circuit between electrical contacts 116 and 118, and a closed circuit between electrical contacts 122 and 124 would produce a binary code of (1, 1).

Figure 5C:
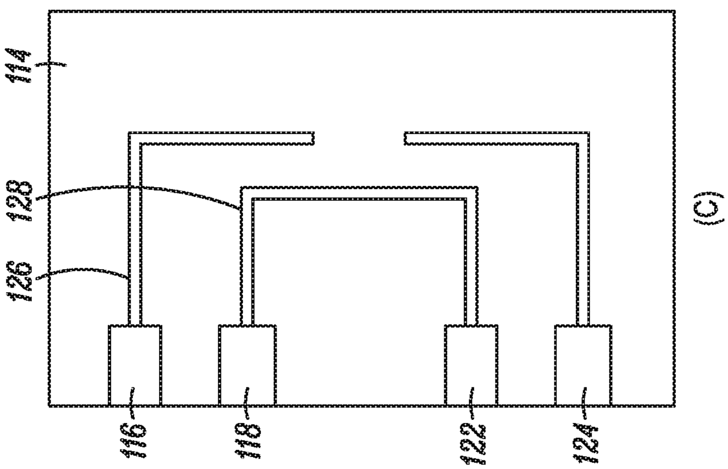
FIGS. 5A-C are exemplary illustrations of electrical contacts and conductors printed on a circuit board.
Figure 5B:
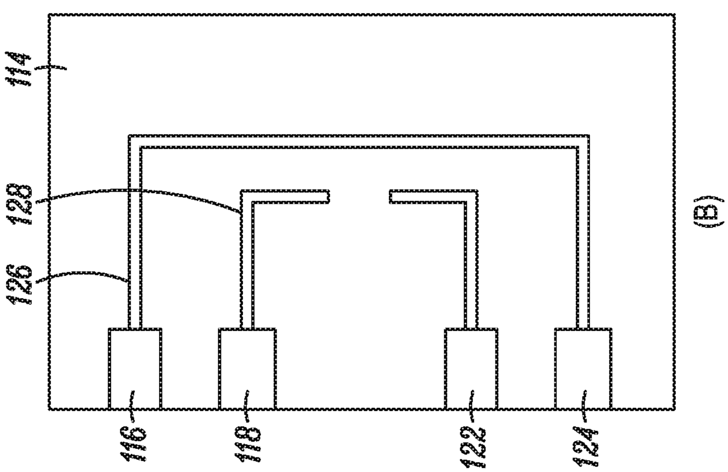
Figure 5A:
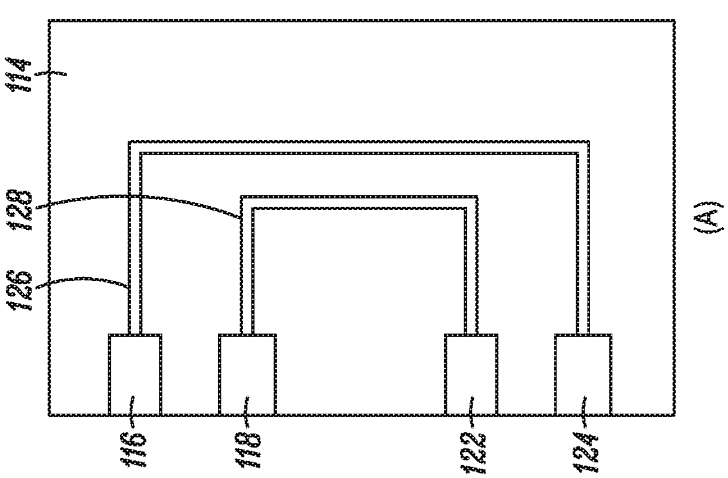

FIGS. 5A-5C illustrate additional configurations of a circuit board 114 having four electrical contacts and two conductors. As seen in FIG. 5A, the electrical contacts 116 and 124 are electrically connected by the conductor 126, and electrical contacts 118 and 122 are electrically connected by the conductor 128. In FIG. 5B, electrical contacts 116 and 124 are electrically connected by the conductor 126, whereas electrical contacts 118 and 122 are not electrically connected. In FIG. 5C, electrical contacts 116 and 124 are not electrically connected, whereas electrical contacts 118 and 122 are electrically connected by the conductor 128. These additional configurations could each produce different codes for identifying a characteristic of the medical device accessory.

As shown, the conductor 128 in FIG. 5B and the conductor 126 in FIG. 5C do not provide an electrical connection between electrical contacts. In other words, the circuits between the respective electrical contacts are open. The specific arrangement of these open circuits may indicate a specific characteristic of the medical device accessory. Alternatively, if a conductor initially provides an electrical connection between the respective electrical contacts and is subsequently severed, an indication may be provided that the medical device accessory has previously been used.

As noted above, it is envisioned that the circuit board could include a significantly larger number of electrical contacts, and any number of conductors could form electrical connections between the electrical contacts. Furthermore, it is envisioned that a single conductor could electrically connect more than two electrical contacts. In this way, numerous conductor patterns, or arrangements of electrical contacts receiving a voltage from the medical device, may be provided. These conductor patterns may indicate the presence and/or whether the medical device accessory has previously been used, as well as other characteristics of the medical device accessory. Depending on the number of electrical contacts and electrical connections provided on a single medical device accessory, it is envisioned that any number of characteristics may be identified by the medical device accessory's conductor pattern For example, the indicated characteristic(s) may comprise the presence of a medical device accessory, whether the medical device accessory is properly connected to the medical device, a prior use of the medical device accessory, the identity of the medical device accessory, the compatibility of the medical device accessory with the medical device, or an operating parameter of the medical device for administration of a medical treatment using the medical device accessory. In the case of a tubing set, the conductor pattern(s) may indicate the presence of the tubing set, correct connection of the tubing set, a prior use of the tubing set, specifications of the tubing set (e.g., manufacturer, lumen diameter, length, etc.), compatibility of the tubing set, or an operating parameter of the medical device (e.g., fluid flow rate, fluid pressure, fluid temperature, etc.).

Figures 6, 7:
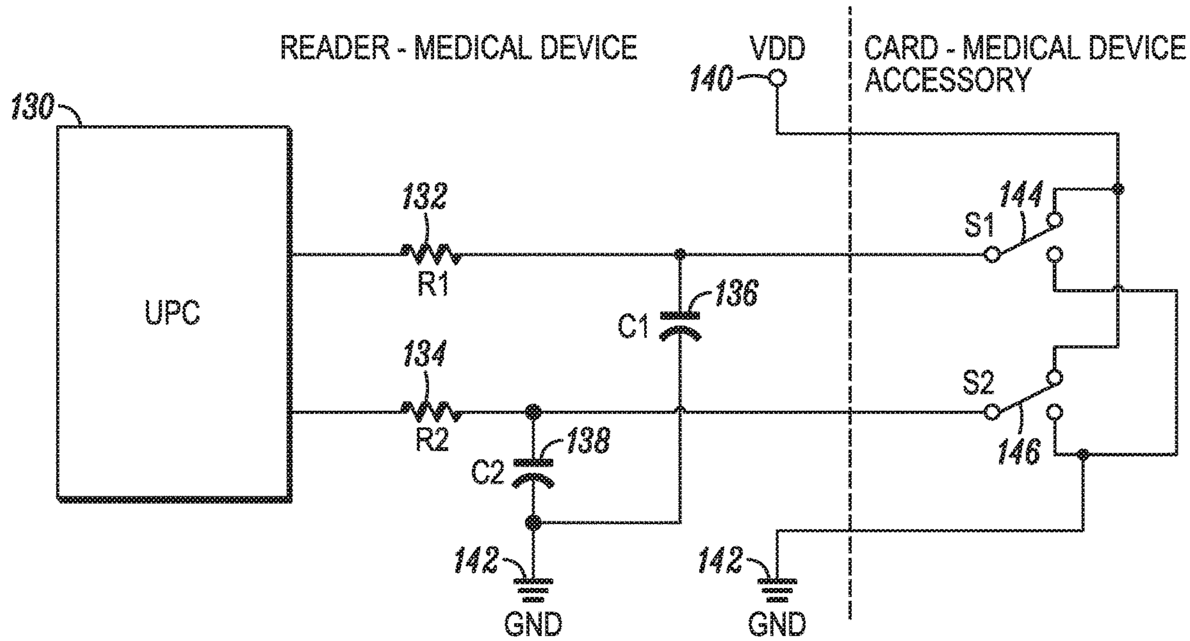
FIG. 6 is a diagram illustrating a circuit formed by a medical device accessory connected with a medical device.
FIG. 7 is a chart showing the logic states of the switches in the circuit of FIG. 6.

Turning to FIG. 6, an exemplary circuit diagram representing the present system is shown. The circuit shown in FIG. 6 is intended to illustrate a medical device accessory having a circuit board with four electrical contacts and two conductors, such as shown in FIGS. 5A-5C, and a medical device adapted to receive the same. The medical device forms the portion of the circuit to the left of the dashed line in FIG. 6, whereas the medical device accessory forms the portion of the circuit to the right of the dashed line in FIG. 6.

The reader portion of the circuit includes a controller 130 (e.g., a microprocessor), a first resistor 132 (labeled R1), a second resistor 134 (labeled R2), a first capacitor 136 (labeled C1), a second capacitor 138 (labeled C2), a power supply 140 or voltage source (labeled VDD), and a ground 142 (labeled GND). The resistors 132 and 134 are used for current limiting. The capacitors 136 and 138 are used to store the state of the respective wires for reading by the controller 130, and may be omitted if the controller 130 is fast enough to read the port pins while using the port's own gate capacitance for storing the state.

The card portion of the circuit is illustrated in the form of a first switch 144 (labeled S1) and a second switch 146 (labeled S2). Although the medical device accessory does not include actual physical switches, the first switch 144 and the second switch 146 are shown in the circuit diagram of FIG. 6 to represent the electrical connections the conductors could make between electrical contacts to accomplish a logic state. As previously mentioned, the medical device accessory does not include any active components.

The potential logic states for "switches" 144 and 146 are shown in FIG. 7. The logic states for the first switch 144 is shown in the first column 148 of FIG. 7. The logic states for the second switch 146 are shown in the second column 150 of FIG. 7. Each of the switches 144 and 146 may be in an up position, a middle (floating) position, or a down position. The up position attaches the switch to the power source 140. The down position attaches the switch to the ground 142. The middle, or floating, position leaves the switch open, making no contact with the power source 140 or the ground 142. Because this approach yields three states for each conductor, a two conductor embodiment, with two contacts per conductor, will yield the 9 logic states shown in FIG. 7.

In this embodiment, it is envisioned that a binary code, as discussed above, may be used to identify electrical connections between any two electrical contacts. Alternatively, a ternary coding scheme, representing the three logic states, may be applied to the "switches" 144 and 146 to identify the electrical connections between the electrical contacts.

Figure 8:
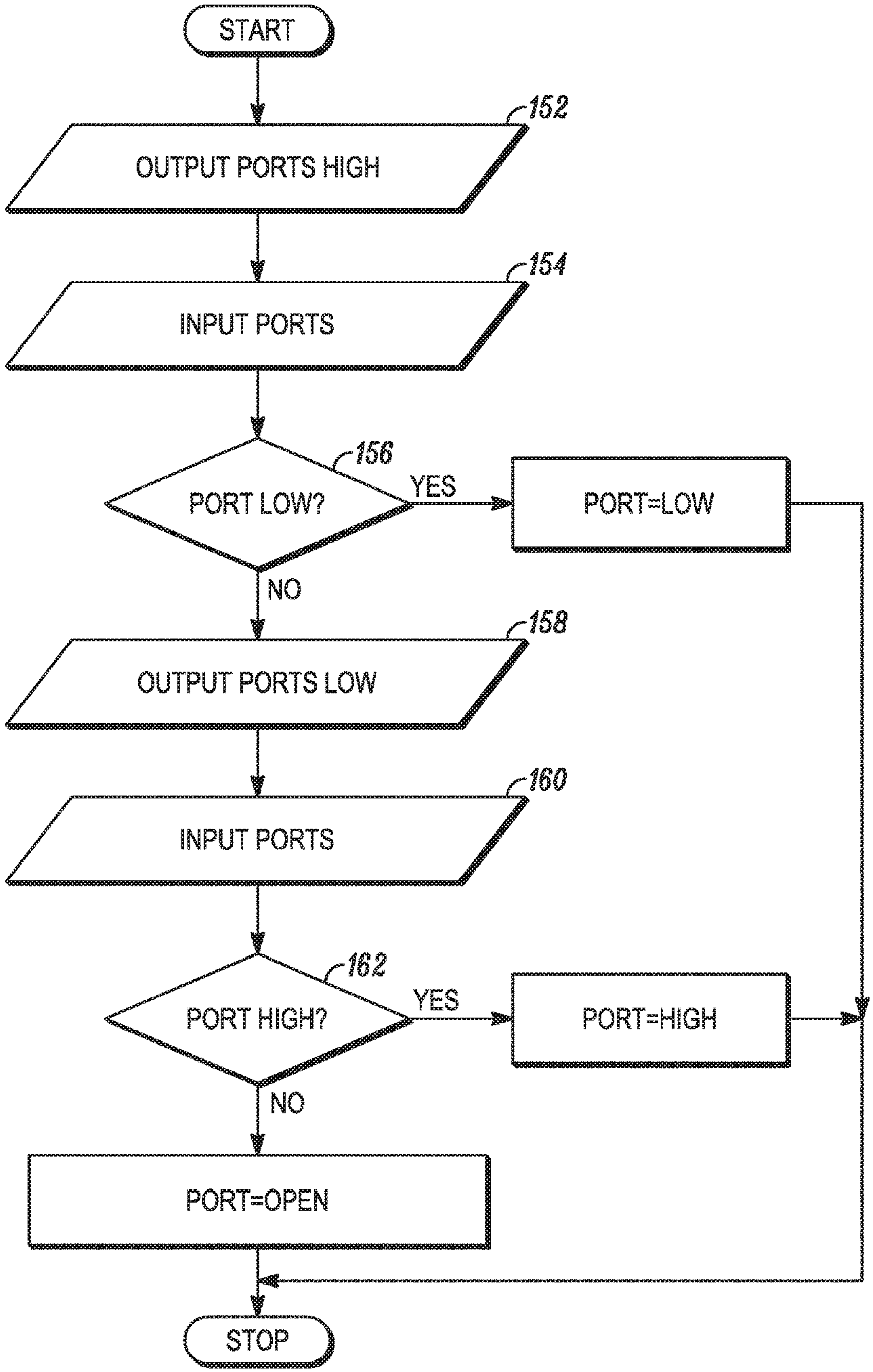
FIG. 8 is a flow chart illustrating the reading process performed by a controller in the circuit of FIG. 6.

Reading for each switch, i.e., each port of the controller 130, is performed as illustrated in the flow chart of FIG. 8. Because the medical device does not know how the contacts are connected until after cycling through the reading process illustrated in FIG. 8, and because a user can change the medical device accessory at any time, in one embodiment, the controller on the medical device may automatically strobe through the contacts on its receptacle periodically, according to the example of FIG. 8, to determine what medical device accessory is attached or not.

In step 152, the ports of the controller are driven High (VDD), which charges the capacitors 136 and 138. In step 154, the ports of the controller 130 are then configured as inputs. In step 156, the controller 130 reads the state of the port pins, and if a port pin is read as being Low (GND), then the position of the corresponding switch must be Low. In other words, because the controller 130 provided a High signal to charge the capacitor, the capacitor would have remained High if the switch were floating or connected to VDD.

Next, in step 158, the ports of the controller are driven Low. In step 160, the controller 130 configures the port pins as inputs. In step 162, the controller 130 then reads the state of the port pins, and if a port pin is read as being High, then the position of the switch must be High. In other words, because the controller 130 provided a Low signal, the capacitor would have remained low if the switch were floating or connected to GND. Consequently, if the input pin corresponding to a switch changed each time the port pin was driven, then the state of the switch must be floating.

The equivalent circuit of FIG. 6 and the associated state table of FIG. 7 relates to a circuit board with 2 conductors, each having 2 contacts, such as that shown in FIGS. 3 and 5. Each conductor, when attached to the medical device, could be measured by the medical device reader/adapter as High (VDD), Low (GND) or Floating (severed). As each conductor could represent 3 possible states, the number of possible states for the combination is 9 (i.e., $3^2$). Because the circuit board 114 is passive, in the sense that there is no active switch or other component, the manufacturer of the medical device accessory having the circuit board 114 can manufacture the medical device accessory with a particular combination of conductor-contact connections to identify that particular type or version of medical device accessory to the medical device.

Figure 9:
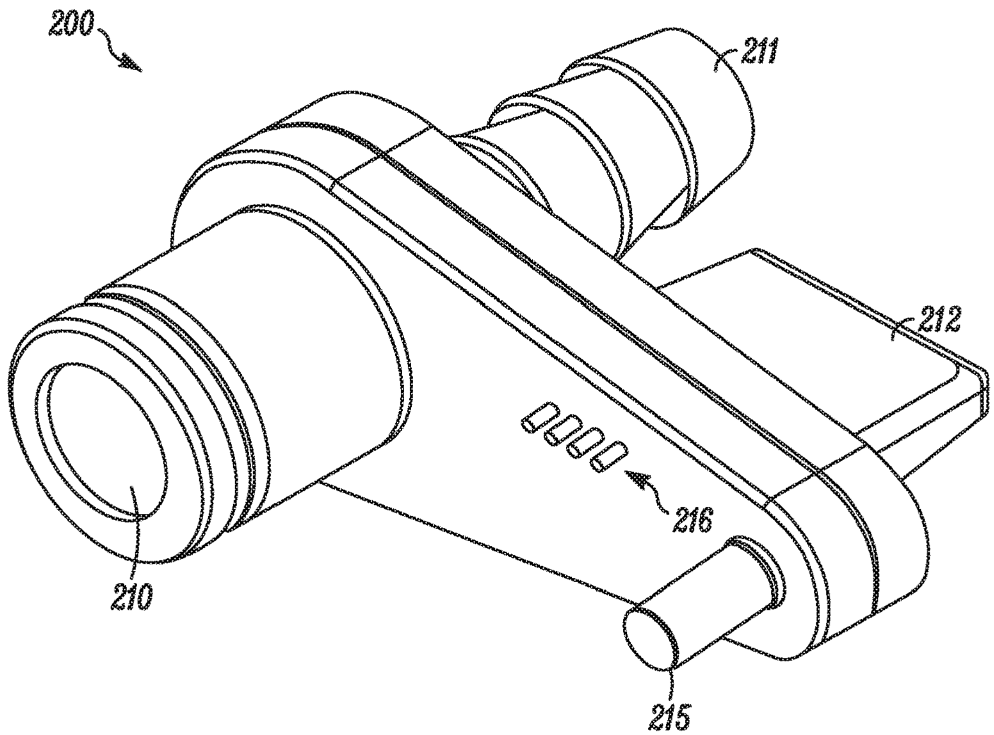
FIG. 9 is a perspective view of an alternative embodiment of a medical device accessory.

Turning to FIG. 9, a perspective view of an alternative embodiment of a medical device accessory 200 is shown. In this embodiment, the medical device accessory 200 is adapted to connect a medical device to another medical device accessory, i.e., as an intermediate connector. For example, the medical device accessory 200 is adapted to connect a pre-existing tubing set with a medical device. However, like the medical device accessory 100, the medical device accessory 200 may be adapted to connect any number of different medical device accessories with any number of medical devices without departing from the principles and concepts described herein.

The medical device accessory 200 shown in FIG. 9 comprises an interface, in the form of a port 210, for engaging a medical device, and a barbed nipple 211 adapted to engage a medical tubing set (not shown). The medical device accessory 200 further includes an electrical housing 212 for housing a circuit board (not shown), and a plurality of electrical contacts 216 extending therefrom. The electrical contacts 216 on the medical device accessory 200 are presented in the form of pins, however any other suitable form of electrical contacts may be used. The medical device accessory 200 further includes a positioning post 215 for insuring proper alignment of the medical device accessory 200 upon its connection with a medical device, such that the plurality of electrical contacts 216 engage corresponding electrical contacts on the medical device. The medical device 200 is otherwise used and operated as described in relation to the above embodiments.

Figure 10:
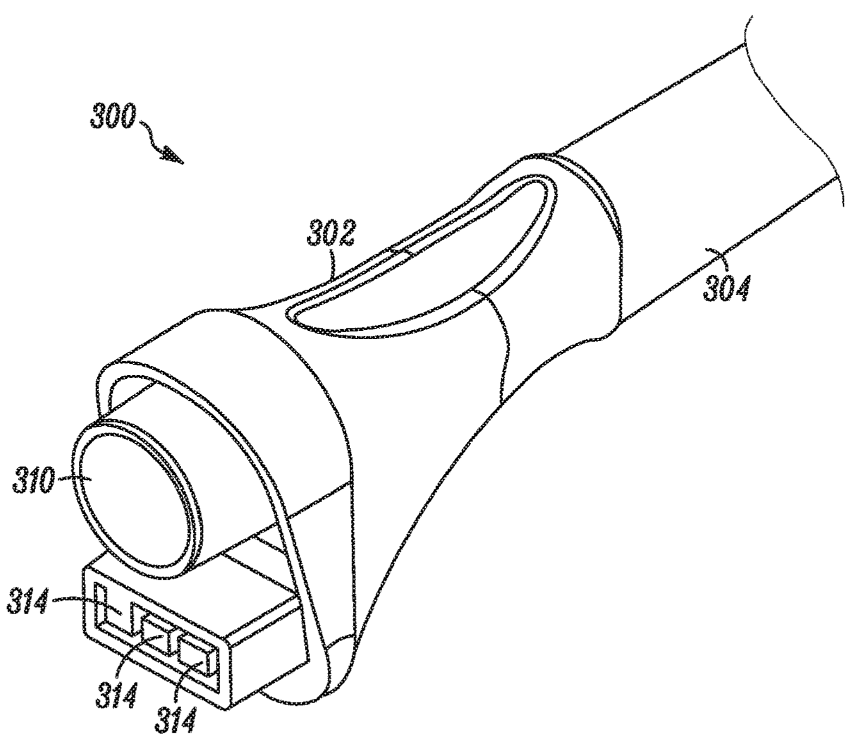
FIG. 10 is a perspective view of another embodiment of a medical device accessory; and, FIG. 11 is a perspective view of an identification device for use with the medical device accessory of FIG. 10.
Figure 11:
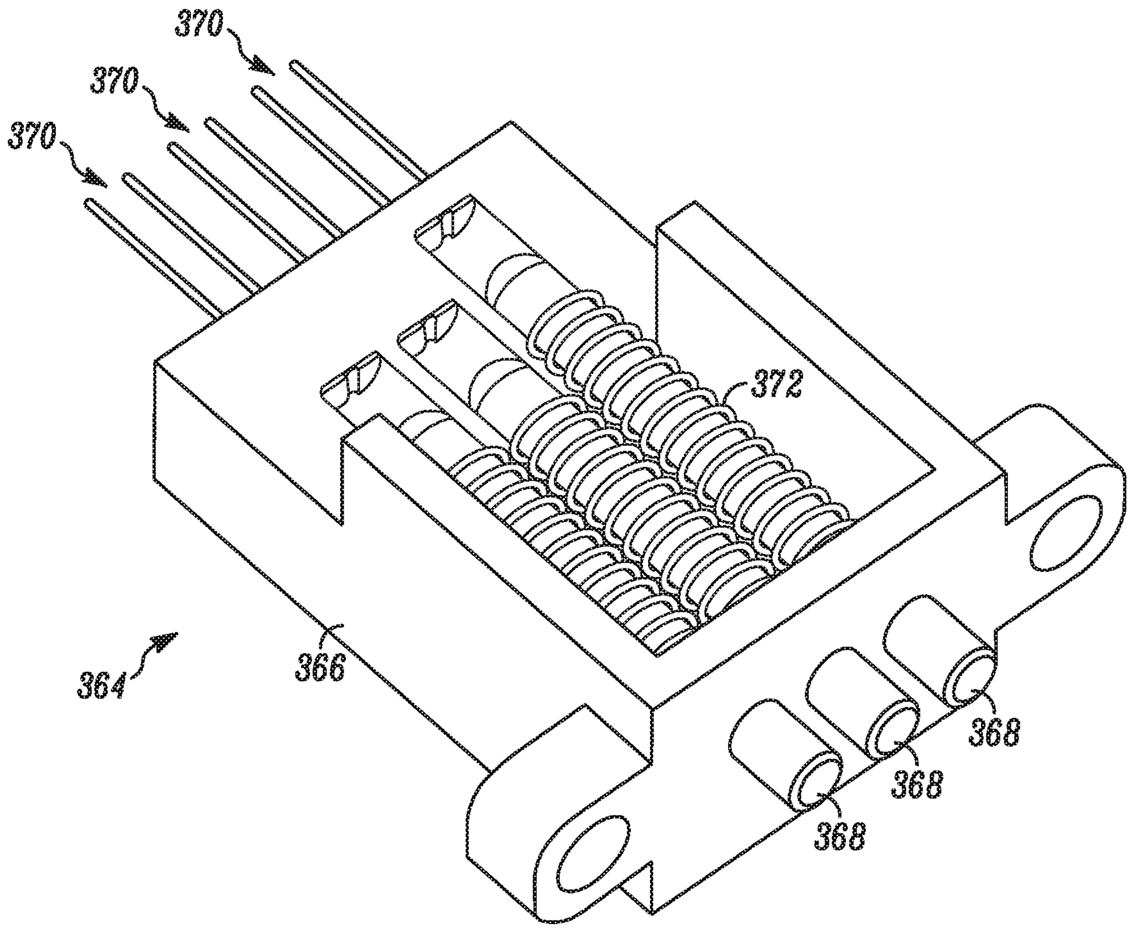

Referring to FIGS. 10 and 11, another embodiment of a medical device accessory 300 and an identification device 364 is shown. Although the following description refers to an embodiment wherein the medical device accessory 300 is a medical tubing set, as with the previously described embodiments, those skilled in the art will appreciate that the disclosed concepts and principles may be applied to any medical device accessory, or may be embodied in a separate accessory adapted to connect a medical device to another medical device accessory, i.e., as an intermediate connector. As described below, the identification device 364 may be associated with a medical device and is adapted for use with the medical device accessory 300. However, it will be appreciated that the medical device accessory 300 may be useable with other suitable identification means associated with all types of medical devices.

Notably, the medical device accessory 300 provides a way to communicate the presence and characteristics of the medical device accessory 300 to a medical device without the use of any electrical or active elements located on the medical device accessory 300. Rather, as explained below, the system can be implemented with inexpensive manufacturing and the inclusion of various structural features on the medical device accessory 300. This system, like the previously described system, has in comparison to the prior art, ease of manufacture, very low cost, multiple configurations, an inexpensive means for disabling use of the accessory, basic electronics for measuring voltage or current, and ease of programming using basic binary concepts.

In general, the medical device accessory 300 is comprised of a connector 302 disposed at an end of a tube 304. The connector may include a female end 306 for receiving the tube 304, a conduit (not shown) running through the connector 302, and a male end 310 adapted to engage a suitable corresponding connection on a medical device, for example, a tubing nipple or a luer. It is envisioned that the connector 302 may be separate from the tube 304, or the connector 302 may be integrally formed with medical device accessory.

The connector 302 further comprises a housing 312. Preferably, the housing 312 is proximate to the interface, i.e., the male end 310 of the connector 302, such that the connection of the medical device accessory 300 with the medical device is unobtrusive. As shown in FIG. 10, three tabs 314 are disposed within the housing 312. Although the connector 302 in FIG. 10 is shown with three tabs 314, it is envisioned that the connector 302 may have as few as one tab 314, or many more tabs 314, for example, positioned in multiple rows. Furthermore, although the tabs 314 in FIG. 10 are positioned side-by-side, it is envisioned that the tabs 314 may be displaced relative to one another to create numerous unique arrangements.

One or more of the tabs 314 may also be configured to break when a threshold insertion pressure is applied to the tab 314 upon connection of the medical device accessory 300 with a medical device. As used herein, the term "break" or "breakable" should be broadly interpreted to include all forms of breaking, including for example, deflecting, bending, stretching, tearing, shattering, removal, etc., and any other change in the structural integrity of a tab 314 such that a tab 314 is no longer able to withstand the threshold pressure. In this way, detection of a broken tab 314 by a medical device may indicate a prior use of the medical device accessory 300. For example, if the connector 302 is made of plastic via a molding operation, the web strength of one or more particular tabs 314 may be selected so that they are breakable upon connection of the medical device accessory 300 with a medical device.

As noted above, the connector 302 is useable with the identification device 364, which may be positioned on the medical device proximate a point of connection for the medical device accessory 300. In general, the identification device 364 of FIG. 11 comprises a housing 366, an arrangement of three switching elements 368, and three pairs of pins 370. The housing 366 of the identification device 364 is shown in FIG. 11 independent of a medical device, however it is envisioned that the identification device 364 and the housing 366 may be formed integrally with a medical device, or as a component that is selectively removable and replaceable.

The switching elements 368 are disposed within the housing 366. A proximal end of each switching element 368 extends beyond the housing 366 and is configured to engage a corresponding tab 314 on the medical device accessory 300, assuming a corresponding tab 314 is provided in the arrangement of tabs 314 on the medical device accessory 300. Attached to the distal end of each switching element 368 is a pair of pins 370.

The switching elements 368 and the pins 370 are configured to slide axially in the distal direction between a first position (as shown in FIG. 11), when the medical device accessory 300 is not connected to the medical device, and a second position (not shown), when the medical device accessory 300 is connected to the medical device and a corresponding tab 314 is provided in the arrangement of tabs 314 on the medical device accessory 300. The switching elements 368, and therefore the pins 370, are biased toward the first position, for example, by a spring 372, positioned concentrically about each switching element 368. Other biasing means may alternatively be used. In this way, the switching elements 368 and the pins 370 are configured to slide from the first position to the second position in response to pressure applied to the switching elements 368 by corresponding tabs 314 on the medical device accessory 300 upon connection of the medical device accessory 300 to the medical device, and to return to the first position upon disconnection of the medical device accessory 300 from the medical device, or alternatively, after a tab 368 breaks upon application of the threshold insertion pressure.

Although the identification device 364 shown in FIG. 11 has three switching elements 368, it is envisioned that the identification device 364 could have as few as one switching element 368, or many more switching elements 368, for example, positioned in multiple rows, such that a switching element 368 corresponds to each tab 314 of the medical device accessory 300. It is also envisioned that the number of switching elements 368 provided within the identification device 364 may be greater than the number of tabs 314 provided on the medical device accessory 300, for example, to accommodate other medical device accessories having a different number or arrangement of tabs 314.

As with the previously described embodiments, the medical device of this system may include a controller and simple circuitry for reading and determining the presence and correctness of the medical device accessory 300, which as previously noted, does not include any electrical or active elements. For example, in the second position, the pins 370 may engage a port on the medical device (not shown) having circuitry similar to that shown in FIG. 6 and described above. By sensing if one or more particular pins 370 have engaged the port (i.e., moved to the second position), if one or more particular pins 370 remain engaged, or if one or more tabs 314 break after engagement, such that the one or more corresponding pins 370 return to the first position, the controller may determine any number of characteristics of the medical device accessory 300, including for example, the presence of the medical device accessory 300, whether the medical device accessory 300 is properly connected, a prior use of the medical device accessory 300, the identity of the medical device accessory 300, the compatibility of the medical device accessory 300 with the medical device, or an operating parameter of the medical device accessory 300 for administration of a medical treatment using the medical device accessory 300. Based on the determination, the system may, for example, provide an indication that the medical device accessory 300 is not present, or that the medical device accessory 300 has previously been used, or that the medical device accessory 300 is not compatible with the medical device, etc. Alternatively, the medical device may, for example, adjust the operating parameters of the medical device for use with the particular medical device accessory 300.

The foregoing description of has been presented for purposes of illustration and description, and is not intended to be exhaustive or to limit the inventions to the precise forms disclosed. It will be apparent to those skilled in the art that the present inventions are susceptible of many variations and modifications coming within the scope of the following claims.

What is claimed is:

1. A medical device accessory comprising:

an interface configured to connect the medical device accessory with an interface of a medical device for administration of a medical treatment using the medical device and the medical device accessory; and a plurality of tabs proximate the interface of the medical device accessory, the plurality of tabs configured to engage one or more switching elements associated with the medical device when the medical device accessory is connected with the medical device;

wherein a spatial arrangement of one or more of the plurality of tabs relative to the one or more switching elements identifies a characteristic of the medical device accessory; and, wherein the medical device accessory is characterized by an absence of an active component.

2. The medical device accessory of claim 1, wherein at least one tab of the plurality of tabs is configured to move at least one switching element from a first position, when the medical device accessory is not connected to the medical device, to a second position, when the medical device accessory is connected to the medical device.

3. The medical device accessory of claim 1, wherein a tab of the plurality of tabs is configured to break when the tab engages with a switching element of the one or more switching elements as the medical device accessory is connected to the medical device to provide an indication of prior use of the medical device accessory.

4. The medical device accessory of claim 1, wherein an arrangement of the plurality of tabs after disconnection of the medical device accessory from the medical device is different than the arrangement of the plurality of tabs upon connection of the medical device accessory with the medical device.

5. The medical device accessory of claim 1, wherein the medical device accessory is characterized by an absence of a resistor, a fuse, a memory chip, a capacitor, an optical sensor, and a radio-frequency identification component.

6. The medical device accessory of claim 1, wherein the plurality of tabs function to identify the characteristic without regard to the interface configured to connect the medical device accessory with the medical device for administration of the medical treatment.

7. The medical device accessory of claim 1, wherein the medical device accessory is operable with the medical device without receipt of power from the medical device.

8. The medical device accessory of claim 1, wherein the medical device is an insufflator.

9. A medical device accessory comprising:

an interface configured to connect the medical device accessory with an interface of a medical device for administration of a medical treatment using the medical device and the medical device accessory;

a plurality of candidate tab locations proximate the interface of the medical device accessory; and at least one tab positioned in at least one of the plurality of candidate tab locations, the at least one tab configured to engage one or more switching elements associated with the medical device when the medical device accessory is connected with the medical device;

wherein a spatial arrangement of the at least one tab relative to the plurality of candidate tab locations identifies a characteristic of the medical device accessory.

10. The medical device accessory of claim 9, wherein each tab of the at least one tab is configured to move a switching element of the one or more switching elements from a first position, when the medical device accessory is not connected to the medical device, to a second position, when the medical device accessory is connected to the medical device.

11. The medical device accessory of claim 9, wherein a tab of the at least one tab is configured to break when the tab engages with a switching element of the one or more switching elements as the medical device accessory is connected to the medical device to provide an indication of prior use of the medical device accessory.

12. The medical device accessory of claim 9, wherein an arrangement of the at least one tab relative to the plurality of candidate tab locations after disconnection of the medical device accessory from the medical device is different than the arrangement of tabs relative to the plurality of candidate tab locations upon connection of the medical device accessory with the medical device.

13. The medical device accessory of claim 9, wherein the medical device accessory is characterized by an absence of an active component.

14. The medical device accessory of claim 9, wherein the medical device accessory is characterized by an absence of a resistor, a fuse, a memory chip, a capacitor, an optical sensor, and a radio-frequency identification component.

15. The medical device accessory of claim 9, wherein the at least one tab functions to identify the characteristic without regard to the interface configured to connect the medical device accessory with the medical device for administration of the medical treatment.

16. The medical device accessory of claim 9, wherein the medical device accessory is operable with the medical device without receipt of power from the medical device.

17. The medical device accessory of claim 9, wherein the medical device is an insufflator.

18. A medical device accessory comprising:

an interface configured to connect the medical device accessory with an interface of a medical device for administration of a medical treatment using the medical device and the medical device accessory; and a tab proximate the interface of the medical device accessory, the tab configured to engage a switching element associated with the medical device when the medical device accessory is connected with the medical device;

wherein the tab is configured to break as the medical device accessory is connected to the medical device to provide an indication of prior use of the medical device accessory.

19. The medical device accessory of claim 18, wherein the tab is configured to move the switching element from a first position, when the medical device accessory is not connected to the medical device, to a second position, when the medical device accessory is connected to the medical device, before the tab is broken.

20. The medical device accessory of claim 18, wherein the medical device accessory is characterized by an absence of a resistor, a fuse, a memory chip, a capacitor, an optical sensor, and a radio-frequency identification component.

21. The medical device accessory of claim 18, wherein the medical device accessory is operable with the medical device without receipt of power from the medical device.

* * * * *